United States Patent [19]

Casagrande et al.

[11] Patent Number: 5,151,414
[45] Date of Patent: Sep. 29, 1992

[54] PHENOXYETHYL AMINE COMPOUNDS ACTIVE ON THE CARDIOVASCULAR SYSTEM

[75] Inventors: Cesare Casagrande, Arese; Gabriele Norcini, Somma Lombardo; Francesco Santangelo, Milan; Claudio Semeraro, Bresso, all of Italy

[73] Assignee: SIMES Societa Italiana Medicinali e Sintetici S.p.A., Vicenza, Italy

[21] Appl. No.: 738,608

[22] Filed: Jul. 31, 1991

Related U.S. Application Data

[60] Division of Ser. No. 659,542, Feb. 22, 1991, Pat. No. 5,070,106, which is a continuation of Ser. No. 288,263, Dec. 22, 1988, abandoned.

[30] Foreign Application Priority Data

Dec. 23, 1987 [IT] Italy ............................ 23183 A/87

[51] Int. Cl.$^5$ .................... C07C 229/38; A61K 31/22; A61K 31/24
[52] U.S. Cl. .................... 514/114; 514/354; 514/356; 514/510; 514/512; 514/533; 514/534; 514/540; 514/546; 514/548; 546/322; 546/326; 558/166; 558/179; 558/186; 558/187; 558/190; 558/269; 558/271; 560/20; 560/32; 560/108; 560/164; 560/252
[58] Field of Search ............... 546/322, 326; 558/166, 558/179, 180, 187, 190, 269, 271; 560/20, 32, 108, 164, 252; 514/354, 356, 114, 510, 512, 533, 534, 540, 546, 548

[56] References Cited

U.S. PATENT DOCUMENTS

| | | | |
|---|---|---|---|
| 4,010,202 | 3/1977 | Sugihara et al. | 564/428 X |
| 4,035,512 | 7/1977 | Sugihara et al. | 564/354 X |
| 4,473,586 | 9/1984 | Debernardis et al. | 564/354 X |
| 4,680,310 | 7/1987 | Hengartner et al. | 564/378 X |

FOREIGN PATENT DOCUMENTS 0026848 4/1981 European Pat. Off.
2528422 12/1983 France.

Primary Examiner—Richard L. Raymond
Attorney, Agent, or Firm—Stevens, Davis, Miller & Mosher

[57] ABSTRACT

Compounds of formula

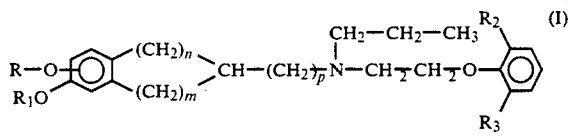

(wherein R, $R_1$, $R_2$, $R_3$, n, m and p have the meanings reported in the specification), their preparation and the compositions for pharmaceutical use containing them as active ingredient are described.

The compounds of formula I have dopaminergic vasodilator activity and they may be used in pharmaceutical field.

8 Claims, No Drawings

PHENOXYETHYL AMINE COMPOUNDS ACTIVE ON THE CARDIOVASCULAR SYSTEM

This is a division of application Ser. No. 07/659,542, filed Feb. 22, 1991, now U.S. Pat. No. 5,070,106 which in turn is a continuation of application Ser. No. 07/288,263, filed Dec. 22, 1988, now abandoned.

The present invention relates to compounds active on the cardiovascular system and more particularly it relates to derivatives of N-propyl-(2-phenoxyethyl)-amine and to their use in the therapeutic field.

Object of the present invention are the compounds of formula:

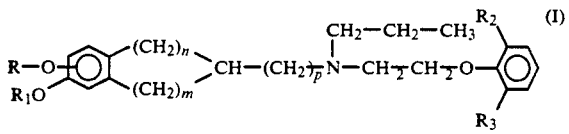

wherein

R and $R_1$, the same or different, represent hydrogen atoms or acyl groups derived from optionally substituted aliphatic, aromatic or heteroaromatic carboxylic acids, from optionally substituted carbamic or carbonic acids, or from phosphoric acid of formula

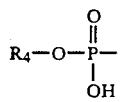

wherein $R_4$ represents a hydrogen atom, a $C_1$-$C_6$ alkyl optionally substituted by one or more groups selected from hydroxy, alkoxy, acyloxy, amino, carboxy and alkoxycarbonyl; or a phenyl; provided that when one of R and $R_1$ represents an acyl derived from phosphoric acid, the other represents a hydrogen atom;

the group O-R is bonded to one of the positions adjacent to the O-$R_1$ group;

n and p represent an integer selected between 0 and 1;

m represents an integer selected from 1, 2, 3 and 4 so that $n+p=1$ and $m+n$ represent an integer selected from 2, 3 and 4;

$R_2$ and $R_3$, the same or different, represent a hydrogen or a halogen atom, an alkyl or an alkoxy group;

and their salts with pharmaceutically acceptable acids.

The compounds of formula I may have one or more asymmetric carbon atoms and they can exist in the form of stereoisomers. Object of the present invention are the compounds of formula I in the form of stereoisomeric mixtures as well as in the form of single stereoisomers.

The compounds of formula I wherein R and $R_1$ represent hydrogen atoms are active on adrenergic and dopaminergic mechanisms carring on vasodilator and hypotensive effects and they may be used in therapy in cardiovascular field for the treatment of hypertension, cardiac decompensation and vascular diseases.

The compounds of formula I wherein one or both substituents R and $R_1$ are different from hydrogen are suitable pro-drugs of the active compounds and they may be used for the same therapeutic purposes.

The reason for the above proviso in the meanings of R and $R_1$ is in the fact that only the mono O-phosphate esters are suitable pro-drugs of the active compounds.

If it is not otherwise specified, the terms alkyl or alkoxy in the compounds of formula I mean a linear or branched alkyl or alkoxy group having from 1 to 4 carbon atoms, specific examples comprise methyl, ethyl, n.propyl, i.propyl, n.butyl, i.butyl, sec.butyl, ter.-butyl, methoxy, ethoxy, n.propoxy, i.propoxy, ter.-butoxy; preferred meanings are methyl and methoxy.

Halogen atoms comprise fluorine, chlorine, bromine or iodine, the first three being preferred.

The term acyl groups derived from aliphatic carboxylic acids means acyl radicals derived from linear or branched aliphatic carboxylic acids having from 1 to 6 carbon atoms, specific examples are the acyl groups derived from the following acids: formic, acetic, propionic, butyric, isobutyric, valeric and pivalic; acyl groups from aromatic or heteroaromatic carboxylic acids derive from optionally substituted benzoic or 2-, 3- or 4-pyridinecarboxylic acid, specific examples comprise benzoyl, 2-pyridinecarbonyl, 3-pyridinecarbonyl, 4-pyridinecarbonyl, 2-chloro-benzoyl, 4-chlorobenzoyl, 2-methyl-benzoyl, 3-methyl-benzoyl, 4-methyl-benzoyl, 2,4-dimethyl-benzoyl, 4-nitro-benzoyl, 4-isobutyryl-benzoyl.

Among the meanings of $R_4$, the term acyloxy means an acyloxy group having from 2 to 4 carbon atoms, a preferred example being acetoxy; the term alkoxycarbonyl means an alkoxycarbonyl group having from 1 to 4 carbon atoms in the alkoxy moiety, specific examples being methoxycarbonyl and ethoxycarbonyl.

Preferred compounds of formula I are those in which $m+n=3$. Pharmaceutically acceptable acids useful for the preparation of salts with the compounds of formula I comprise hydrochloric, hydrobromic, hydriodic, nitric, sulfuric, phosphoric, acetic, benzoic, maleic, fumaric, succinic, tartaric, citric, aspartic and methanesulfonic.

Specific examples of compounds according to the present invention are:

N-[2-(2,6-dichlorophenoxy)-ethyl]-N-propyl-1-aminomethyl-6,7-dihydroxy-1,2,3,4-tetrahydronaphthalene N-[2-(2,6-dichlorophenoxy)-ethyl]-N-propyl-1-aminomethyl-6,7-dihydroxy-1,2,3,4-tetrahydronaphthalene hydrochloride N-[2-(2,6-dichlorophenoxy)-ethyl]-N-propyl-1-aminomethyl-6,7-dihydroxy-1,2,3,4-tetrahydronaphthalene succinate N-[2-(2,6-dimethoxyphenoxy)-ethyl]-N-propyl-1-aminomethyl-5,6-dihydroxy-1,2,3,4-tetrahydronaphthalene N-[2-(2,6-dimethylphenoxy)-ethyl]-N-propyl-1-aminomethyl-5,6-dihydroxy-1,2,3,4-tetrahydronaphthalene N-[2-(2,6-dimethoxyphenoxy)-ethyl]-N-propyl-2-amino-5,6-dihydroxy-1,2,3,4-tetrahydronaphthalene N-[2-(2,6-dimethylphenoxy)-ethyl]-N-propyl-2-amino-5,6-dihydroxy-1,2,3,4-tetrahydronaphthalene N-[2-(2,6-dichlorophenoxy)-ethyl]-N-propyl-2-amino-5,6-dihydroxy-1,2,3,4-tetrahydronaphthalene N-[2-(2,6-dichlorophenoxy)-ethyl]-N-propyl-2-amino-5,6-diacetoxy-1,2,3,4-tetrahydronaphthalene N-[2-(2,6-dichlorophenoxy)-ethyl]-N-propyl-2-amino-5,6-diisobutyryloxy-1,2,3,4-tetrahydronaphthalene N-[2-(2,6-dichlorophenoxy)-ethyl]-N-propyl-2-amino-5-O-dihydrogenphosphate-6-hydroxy-1,2,3,4-tetrahydronaphthalene N-[2-(2,6-dimethylphenoxy)-ethyl]-N-propyl-2-amino-5-O-methylhydrogenphosphate-6-hydroxy-1,2,3,4-tetrahydronaphthalene N-[2-(2,6-dichlorophenoxy)-ethyl]-N-propyl-1-aminomethyl-4,5-dihydroxy-indan N-[2-(2,6-dichlorophenoxy)-ethyl]-N-propyl-1-aminomethyl-5,6-dihydroxy-indan N-[2-(2,6-dichlorophenoxy)-ethyl]-N-propyl-2-amino-4,5-dihydroxyindan N-[2-(2,6-dichlorophenoxy)-ethyl]-N-propyl-2-amino-5,6-dihydroxyindan N-[2-(2,6-dichlorophenoxy)-ethyl]-N-propyl-5-aminomethyl-1,2-dihydroxy-benzocycloheptane N-[2-(2,6-dichlorophenoxy)-ethyl]-N-propyl-5-aminomethyl-2,3-dihydroxy-benzocycloheptane N-[2-(2,6-dichlorophenoxy)-ethyl]-N-propyl-6-amino-1,2-dihydroxy-benzocycloheptane N-[2-(2,6-dichlorophenoxy)-ethyl]-N-propyl-6-amino-2,3-dihydroxy-benzocycloheptane The preparation of the compounds of formula I can be carried out according to different alternative methods, which are described hereinafter.

Useful intermediates for some synthetic methods are the compounds of formula

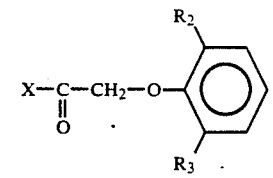
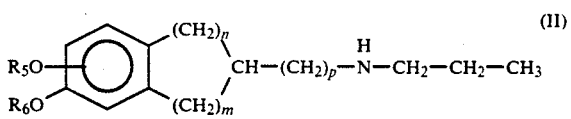

(II)

wherein n, m and p have the above reported meanings;

$R_5$ and $R_6$, the same or different, represent a hydrogen atom or a protective group selected, for example, from methyl and benzyl.

The compounds of formula II are known or they can be prepared according to known methods (J. Cannon et al.—J. Med. Chem., 1983, 26, 813–816 and A. Bradbury et al.—Eur. J. Pharm., 105, 1984, 33–47 and reference cited therein).

Preferably $R_5$ and $R_6$ are the same when the aim of the synthesis is the preparation of compounds of formula I wherein R and $R_1$ are hydrogen atoms, but they may be different when the aim is the preparation of a compound of formula I wherein one of R and $R_1$ is different from hydrogen.

At the end of the synthetic process or before carrying out a reaction on an intermediate, the optional protective groups may be removed by conventional reactions.

For example, when one or both $R_5$ and $R_6$ are methyl, the deprotection of the hydroxy group may be carried out by reaction with halogenidric acids or with boron tribromide; when one or both $R_5$ and $R_6$ are benzyl groups, the deprotection of the hydroxy group may be carried out by hydrogenolysis.

The compounds of formula II are useful starting compounds in three different synthetic methods:

a) the first method consists in a reaction between compound II and a halide of a suitable phenoxyacetic acid of formula

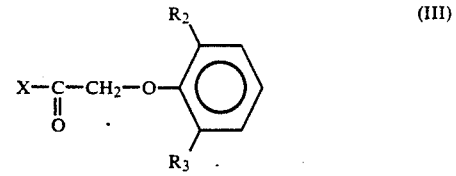

(III)

wherein $R_2$ and $R_3$ have the meanings reported for formula I and X represents a chlorine or a bromine atom.

The reaction is carried out in an inert solvent in the presence of a base which acts as a halogenidric acid acceptor such as an alkaline carbonate or bicarbonate, a tertiary amine (triethylamine or pyridine). In the last case the amine may act also as a solvent.

Through the above reaction the intermediates of formula

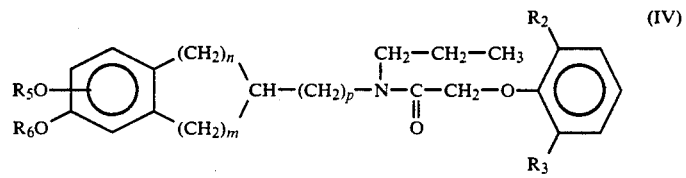

(IV)

wherein $R_2$, $R_3$, $R_5$ and $R_6$, n, m and p have the above reported meanings, are obtained.

The reduction of the amidic carbonyl in the compounds of formula IV, preceded or followed by the optional deprotection of the hydroxy groups from the protective groups $R_5$ and $R_6$, gives the compounds of formula I wherein R and $R_1$ are hydrogen atoms.

The reduction of the compounds of formula IV may be carried out with electrophilic reducing agents, particularly diborane optionally complexed with dimethylsulfide, tetrahydrofuran, aliphatic amines such as triethylamine or aromatic amines such as N,N-diethylaniline or pyridine.

Alternatively, the reduction may be carried out with nucleophilic reducing agents such as metal hydrides, for example lithium aluminum hydride and sodium (2-methoxyethoxy)-aluminum hydride.

The reaction is carried out in the presence of a solvent inert under the reaction conditions such as for example tetrahydrofuran, diethylether or 1,2-dimethoxyethane.

b) Alternatively, instead of the acyl halide III a phenoxyacetic aldehyde of formula

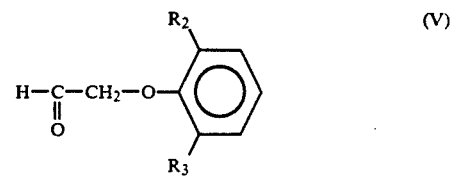

(V)

wherein $R_2$ and $R_3$ have the above reported meanings, may be used.

By reaction with compound II, carried out in an inert solvent and in the presence of dehydrating agents such as molecular sieves, and by a subsequent reduction according to conventional methods, the compounds of formula I wherein R and $R_1$ are hydrogen atoms or their precursors, when $R_5$ and $R_6$ are different from hydrogen, are obtained.

The reduction is carried out in an inert solvent by catalytic hydrogenation or by reaction with reducing agents such as sodium borohydride, sodium cyanoborohydride and lithium aluminumhydride.

c) Another process for the preparation of the compounds of formula I consists in the condensation between a compound of formula II and a compound of formula

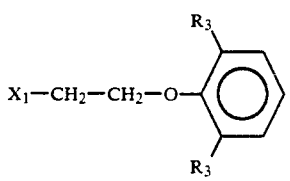

(VI)

wherein $R_2$ and $R_3$ have the above reported meanings and $X_1$ represents a leaving group such as a chlorine or a bromine atom or an alkylsulfonyloxy or arylsulfonyloxy group.

The reaction is carried out in an inert solvent and in the presence of a base and it gives directly the compounds of formula I wherein R and $R_1$ are hydrogen atoms or their precursors, when in the used compound of formula II $R_5$ and $R_6$ are different from hydrogen.

Further two alternative processes for the synthesis of the compounds of formula I, using intermediates different from the compounds of formula II, are the following:

d) A process uses as starting product a compound of formula

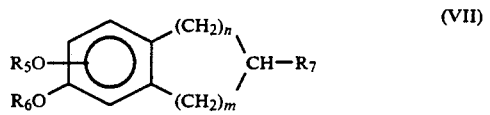

(VII)

wherein
$R_5$ and $R_6$, m and n have the above reported meanings and $R_7$ represents a formyl group or a $(CH_2)_p$—Y group wherein Y represents a halogen atom or an alkylsulfonyloxy or arylsulfonyloxy group;
which is condensed with a secondary amine of formula

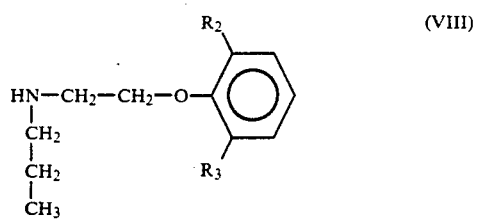

(VIII)

wherein $R_2$ and $R_3$ have the above reported meanings; by working in a way similar to what described in paragraph b. The compounds of formula I wherein p=1, R and $R_1$ are hydrogen atoms or their precursors when $R_5$ and $R_6$ are different from hydrogen are obtained.

e) Alternatively, the amines of formula

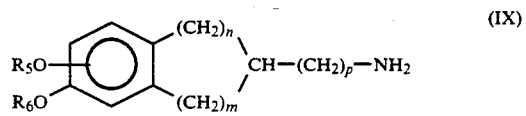

(IX)

wherein $R_5$, $R_6$, n, m and p have the above reported meanings; may be used to obtain, following one of the synthetic methods described in paragraphs a, b or c, the intermediate of formula

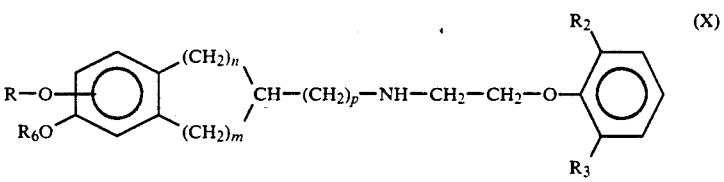

(X)

wherein $R_2$, $R_3$, $R_5$, $R_6$, n, m, and p have the above reported meanings.

This intermediate (X), by a subsequent alkylation with a propyl halide in a suitable organic solvent and optionally in the presence of a base, gives the compounds of formula I wherein R and $R_1$ are hydrogen atoms or their precursors wherein $R_5$ and $R_6$ are different from hydrogen.

The compounds of formula III, V, VI, VII, VIII and IX are known or they can be easily prepared by known methods. The above described different synthetic methods are all substantially equivalent as far as their comparable yield and their versatility are concerned.

By working according to the above described methods the compounds of formula I in which R and $R_1$ represent hydrogen atoms or in which one or both the aromatic hydroxy groups are in a protected form (for example as methylether or benzylether) are prepared.

The compounds of formula I in which both aromatic hydroxy groups are free (R=$R_1$=H) or one is protected (preferably in the form of benzylether) are also the starting compounds for the preparation of the compounds of formula I in which one or both R and $R_1$ are different from hydrogen.

The preparation of the compounds of formula I in which one or both R and $R_1$ are acyl groups derived from aliphatic or aromatic carboxylic acids is carried out by acylation according to conventional methods, for example with a suitable acyl halide or with an anhydride, or, when one of R and $R_1$ represents a group of formula

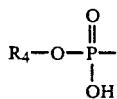

and, in other words, for the compounds of formula I wherein one of the hydroxy group is esterified by phosphoric acid or a derivative thereof, the monophosphorylation method described in the European Patent Application No. 167204 in the name of Simes S.p.A. to which it is referred as far as both the reagents and the experimental conditions are concerned, is used.

The compounds of formula I in an optically active form are obtained by optical separation or by stereoselective or stereospecific synthesis.

The preparation of the salts of the compounds of formula I with pharmaceutically acceptable acids is carried out according to usual methods.

A suitable method consists in adding the selected acid to a solution of compound I in a solvent from which the obtained salt precipitates and can be separated by filtration. As above reported, the compounds of formula I are endowed with dopaminergic vasodilator activity and they may be used in therapy in hypertension, in cardiac insufficiency and in cerebral and peripheral vascular diseases.

In fact, the compounds object of the present invention reduce meaningfully systemic arterial pressure after administration by intravenous route in anesthetized dog (see example 11).

Furthermore, the compounds of formula I show a remarkable dopaminergic activity in addition to an $\alpha_1$-antagonistic effect. The dopaminergic activity has been evaluated by receptor binding tests as "in vitro" receptor affinity on isolated membranes of rat striated muscle and by pharmacological tests as "in vitro" inhibition of the answer to electric stimulation of cat right atrium. The obtained $IC_{50}$ values are 251 nM and 8.5 $\mu$M respectively for compound N-[2-(2,6-dichlorophenoxy)-ethyl]-N-propyl-2-amino-5,6-dihydroxy-1,2,3,4-tetrahydronaphthalene hydrochloride (hereinafter referred to as compound A).

The $\alpha_1$-antagonistic activity has been evaluated as receptor binding on rat cerebral cortex and as antagonism to contraction induced by phenylephrine ($\alpha_1$-agonist) on rabbit aorta. In these tests compound A has shown an $IC_{50}=76$ nM (receptor binding) and a $pA_2=7.42$ (rabbit aorta).

For the practical administration, the compounds of formula I can be preferably prepared in the form of a pharmaceutical composition suitable for the selected administration route.

The pharmaceutical compositions containing the compounds of formula I, or their pharmaceutically acceptable salts, together with one or more solid or liquid, organic or inorganic pharmaceutical excipients and optionally further additives such as diluents, preserving agents, moistening agents, colouring agents and flavouring agents are a further object of the present invention.

The pharmaceutical compositions object of the invention can be administered in the form of solid pharmaceutical preparations, such as tablets, coated tablets, capsules, granulates and suppositories, or in the form of liquid pharmaceutical preparations such as syrups, suspensions, emulsions and solutions suitable for oral or parenteral administration.

The compounds object of the present invention can be formulated also in the form of slow and protracted release pharmaceutical preparations.

The preparation of the pharmaceutical compositions object of the present invention can be carried out according to usual techniques.

In order to better illustrate the present invention, the following examples are now given.

EXAMPLE 1

Preparation of
1-[N-propyl-(2,6-dichlorophenoxy)acetamidomethyl]-6,7-dihydroxy-1,2,3,4-tetrahydronaphtalene To a solution of 1-(n.propylamino)-methyl-6,7-dihydroxy-1,2,3,4-tetrahydronaphtalene hydrobromide (6 g; 0.019 moles) and triethylamine (9.9 ml) in dimethylformamide (120 ml) (2,6-dichlorophenoxy)-acetyl chloride (5.6 g; 0.023 moles) was added at room temperature.

The reaction mixture was heated at 60° C. and after 5 hours the solvent was evaporated.

The residue was dissolved in ethyl acetate; the organic phase was washed with water and dried on sodium sulphate. After evaporation of the solvent, the obtained crude was purified by column chromatography on silica gel (eluent methylene chloride:ethylacetate=98:2) giving 1-[N-propyl-(2,6-dichlorophenoxy)acetamidomethyl]-6,7-dihydroxy-1,2,3,4-tetrahydronaphtalene as a chromatographically pure oil (thin layer chromatography, eluent methylene chloride:ethyl acetate=98:2)

$^1$H-NMR (60 MHz-CDCl$_3$): delta (ppm): 0.9 (3H, s); 1.95 (6H, m); 2.66 (2H, m); 6.9 (5H, m).

By working in a similar way the following compounds were prepared:

1-[N-propyl-(2,6-dimethoxyphenoxy)-acetamidomethyl]-5,6-dibenzyloxy-1,2,3,4-tetrahydronaphthalene chromatographically pure oil (thin layer chromatography, eluent methylene chloride:ethyl acetate=90:10)

$^1$H-NMR (60 MHz-CDCl$_3$): delta (ppm): 0.3 (3H, t); 2.08 (2H, m); 2.76 (2H, m); 3.4 (2H, t); 3.73 (3H, s); 3.85 (3H, s); 4.63 (4H, m); 5.03 (2H, s); 5.2 (2H, s); 6.5–7.5 (15H, m).

1-[N-propyl-(2,6-dimethylphenoxy)-acetamidomethyl]-5,6-dibenzyloxy-1,2,3,4-tetrahydronaphthalene chromatographically pure oil (thin layer chromatography, eluent methylene chloride:ethyl acetate=95:5)

$^1$H-NMR (60 MHz-CDCl$_3$): delta (ppm): 2.15 (6H, s); 4.05 (2H, s); 4.1 (2H, s); 6.0 (4H, m); 6.5 (12H, m).

EXAMPLE 2

Preparation of
1-[N-propyl-(2,6-dimethoxyphenoxy)-acetamidomethyl]-5,6-dihydroxy-1,2,3,4-tetrahydronaphtalene To a solution of 1-[N-propyl-(2,6-dimethoxyphenoxy)acetamidomethyl]-5,6-dibenzyloxy-1,2,3,4-tetrahydronaphthalene (3 g; 0.0049 moles), prepared as described in example 1, in absolute ethanol (120 ml) palladium 10% on activated charcoal (1.2 g) was added. The mixture was hydrogenated at room temperature under a pressure of 2-3 hydrogen atmospheres.

After 8 hours the suspension was filtered and the solvent was evaporated obtaining 1-[N-propyl-(2,6-dimethoxyphenoxy)-acetamidomethyl]-5,6-dihydroxy-1,2,3,4-tetrahydronaphtalene as a chromatographically pure oil (thin layer chromatography, eluent methylene chloride:ethyl acetate=9:1).

$^1$H-NMR (60 MHz-DMSO-d$_6$): delta (ppm): 0.8 (3H, t); 1.7 (6H, m); 2.6 (2H, m); 3.5 (5H, m); 3.7 (3H, m); 3.9 (3H, m); 4.2 (1H, s); 4.6 (1H, s); 6.5 (5H, m).

By working in a similar way the following compound was prepared:

1-[N-propyl-(2,6-dimethylphenoxy)-acetamidomethyl]-5,6-dihydroxy-1,2,3,4-tetrahydronaphthalene
chromatographically pure oil (thin layer chromatography, eluent methylene chloride:methanol=9:1)

$^1$H-NMR (60 MHz-CDCl$_3$): delta (ppm): 1.0 (3H, t); 1.8 (3H, m); 2.0 (6H, s); 6.5 (2H, dd); 7.0 (12H, m).

EXAMPLE 3

Preparation of 2-[N-propyl-(2,6-dimethoxyphenoxy)-acetamido]-5,6-dihydroxy-1,2,3,4-tetrahydronaphthalene To a solution of 2-(n.propylamino)-5,6-dihydroxy-1,2,3,4-tetrahydronaphtalene (5 g; 0.023 moles) and triethylamine (3.67 ml) in anhydrous dimethylformamide (100 ml), at room temperature and under nitrogen, a solution of (2,6-dimethoxyphenoxy)-acetyl chloride (4.18 g; 0.018 moles) in anhydrous dimethylformamide (10 ml) was added.

After 3 hours the solvent was evaporated under reduced pressure and the obtained residue was dissolved in ethyl acetate. The solution was washed with diluted HCl, then with water up to neutral pH and the organic phase was dried on sodium sulphate. After evaporation of the solvent, the crude was dissolved in methanol.

To the solution p.toluenensulphonic acid (0.5 g) was added and the mixture was heated under reflux for 8 hours. The solvent was evaporated and the residue was purified by column chromatography on silica gel (eluent methylene chloride:methanol=97:3) giving 2-[N-propyl-(2,6-dimethoxyphenoxy)-acetamido]-5,6-dihydroxy-1,2,3,4-tetrahydronaphthalene with m.p.=157°-158° C. (ethyl acetate).

IR and $^1$H-NMR spectra were consistent with the assigned structure. By working in a similar way the following compounds were prepared:

2-[N-propyl-(2,6-dimethylphenoxy)-acetamido]-5,6-dihydroxy-1,2,3,4-tetrahydronaphthalene
  m.p.=153°-155° C. (ethyl acetate)

2-[N-propyl-(2,6-dichlorophenoxy)-acetamido]-5,6-dihydroxy-1,2,3,4-tetrahydronaphthalene
  m.p.=157°-159° C. (ethyl acetate).

EXAMPLE 4

Preparation of N-[2-(2,6-dichlorophenoxy)-ethyl]-N-propyl-1-aminomethyl-6,7-dihydroxy-1,2,3,4-tetrahydronaphthalene hydrochloride To a mixture of 1-[N-propyl-(2,6-dichlorophenoxy)-acetamidomethyl]-6,7-dihydroxy-1,2,3,4-tetrahydronaphthalene (7.2 g; 0.016 moles), prepared as described in example 1, and sodium borohydride (1.24 g; 0.033 moles) in anhydrous tetrahydrofuran (150 ml), ether borum trifluoride (4.54 g) was added at the temperature of 0°-5° C. and under nitrogen.

After keeping under stirring for 60 minutes at room temperature, the reaction mixture was heated under reflux for 1 hour. After cooling, HCl 6N (6 ml) was added and the mixture was heated under reflux for 30 minutes.

The residue, obtained after evaporation of the solvent, was dissolved in water, neutralized and extracted with ethyl acetate. After drying on sodium sulphate and evaporation of the solvent, the crude was dissolved in ethanol.

By acidification with ethyl ether saturated by HCl, N-[(2,6-dichlorophenoxy)-ethyl]-N-propyl-1-aminomethyl-6,7-dihydroxy-1,2,3,4-tetrahydronaphtalene precipitated as hydrochloride with m.p.=75°-79° C.

IR and $^1$H-NMR spectra were consistent with the assigned structure. By working in a similar way the following compounds were prepared:

N-[2-(2,6-dimethoxyphenoxy)-ethyl]-N-propyl-1-aminomethyl-5,6-dihydroxy-1,2,3,4-tetrahydronaphthalene hydrochloride
  m.p.=73°-77° C. (ethanol/ethyl ether)

N-[2-(2,6-dimethylphenoxy)-ethyl]-N-propyl-1-aminomethyl-5,6-dihydroxy-1,2,3,4-tetrahydronaphthalene hydrochloride
  m.p.=160°-165° C. (ethyl acetate)

N-[2-(2,6-dimethoxyphenoxy)-ethyl]-N-propyl-2-amino-5,6-dihydroxy-1,2,3,4-tetrahydronaphthalene hydrochloride
  m.p.=100°-104° C. (water)

N-[2-(2,6-dimethylphenoxy)-ethyl]-N-propyl-2-amino-5,6-dihydroxy-1,2,3,4-tetrahydronaphthalene hydrochloride
  m.p.=210°-214° C. (water)

N-[2-(2,6-dichlorophenoxy)-ethyl]-N-propyl-2-amino-5,6-dihydroxy-1,2,3,4-tetrahydronaphthalene hydrochloride
  m.p.=169°-174° C. (water).

EXAMPLE 5

Preparation of N-[2-(2,6-dichlorophenoxy)ethyl]-N-propyl-2-amino-5,6-diisobutyryloxy-1,2,3,4-tetrahydronaphthalene hydrochloride To a solution of N-[2-(2,6-dichlorophenoxy)-ethyl]-N-propyl-2-amino-5,6-dihydroxy-1,2,3,4-tetrahydronaphthalene hydrochloride (1 g; 0.00224 moles), prepared as described in example 4, in pyridine (10 ml), kept at 15° C., isobutyrylchloride (0.58 ml) was added. After 3 hours the solution was evaporated and the residue, dissolved in chloroform and washed several times with water, was purified by column chromatography on silica gel (eluent methylene chloride:ethyl acetate=95:5).

N-[2-(2,6-dichlorophenoxy)ethyl]-N-propyl-2-amino-5,6-diisobutyryloxy-1,2,3,4-tetrahydronaphthalene hydrochloride was so obtained.
  m.p.=198°-199° C. (ethyl acetate).

By working in a similar way the following compounds were prepared:

N-[2-(2,6-dichlorophenoxy)-ethyl]-N-propyl-2-amino-5,6-di-(4-isobutyryloxy-benzyloxy)-1,2,3,4-tetrahydronaphthalene
  m.p.=84°-86° C. (isopropyl ether)

N-[2-(2,6-dichlorophenoxy)-ethyl]-N-propyl-2-amino-5,6-di-(2,2-dimethyl-propanoyloxy)-1,2,3,4-tetrahydronaphthalene hydrochloride
  m.p.=195°-199° C. (ethyl acetate)

N-[2-(2,6-dichlorophenoxy)-ethyl]-N-propyl-2-amino-5,6-di-(dimethylcarbamoyloxy)-1,2,3,4-tetrahydronaphthalene hydrochloride
  m.p.=95°-110° C. (ethyl ether)

N-[2-(2,6-dichlorophenoxy)-ethyl]-N-propyl-2-amino-5,6-di-ethoxycarbonyloxy-1,2,3,4-tetrahydronaphthalene hydrochloride
m.p.=140°-143° C. (ethyl acetate).

EXAMPLE 6

Monophosphorylation of N-[2-(2,6-dichlorophenoxy)-ethyl]-N-propyl-2-amino-5,6-dihydroxy-1,2,3,4-tetrahydronaphthalene hydrochloride Phosphoric acid 85% (0.66 g) was added to phosphoric anhydride (0.78 g), the mixture was heated at 150° C. for 1.5 hours, then was cooled at room temperature and N-[2-(2,6-dichlorophenoxy)-ethyl]-N-propyl-2-amino-5,6-dihydroxy-1,2,3,4-tetrahydronaphthalene hydrochloride (0.17 g; 0.38 mmoles), prepared as described in example 4, was added.

After 24 hours water and ice were added and the separated product was filtered and crystallized from water giving a mixture of N-[2-(2,6-dichlorophenoxy)-ethyl]-N-propyl-2-amino-5-hydroxy-6-O-dihydrogenphosphate-1,2,3-4-tetrahydronaphthalene hydrochloride and N-[2-(2,6-dichlorophenoxy)-ethyl]-N-propyl-2-amino-6-hydroxy-5-O-dihydrogenphosphate-1,2,3,4-tetrehydronaphthalene hydrochloride.
m.p.=160°-175° C.

EXAMPLE 7

Preparation of 2-[N-propyl-(2,6-dichlorophenoxy)-acetamido]-6-benzyloxy-5-hydroxy-1,2,3,4-tetrahydronaphthalene and 2-[N-propyl-(2,6-dichlorophenoxy)-acetamido]-5-benzyloxy-6-hydroxy-1,2,3,4-tetrahydronaphthalene A mixture of 2-[N-propyl-(2,6-dichlorophenoxy)-acetamido]-5,6-dihydroxy-1,2,3,4-tetrahydronaphthalene (13 g; 3 mmoles), prepared as described in example 3, sodium bicarbonate (10.2 g) and benzyl chloride (7 ml) in ethanol (20 ml) was heated under reflux for 13 hours.

The mixture was cooled, filtered and evaporated. The residue was dissolved in methylene chloride, washed with water and dried on sodium sulphate.

After evaporation of the solvent a crude was obtained from which 2-[N-propyl-(2,6-dichlorophenoxy)-acetamido]-6-benzyloxy-5-hydroxy-1,2,3,4-tetrahydronaphthalene as a chromatographically pure oil (thin layer chromatography, eluent toluene:methanol=9:1)
$^1$H-NMR (60 MHz-CDCl$_3$): delta (ppm): 0.93 (3H, t); 1.55-2.18 (4H, m); 2.75-3.34 (6H, m); 6.74-7.42 (10H, m).

And 2-[N-propyl-(2,6-dichlorophenoxy)-acetamido]-5-benzyloxy-6-hydroxy-1,2,3,4-tetrahydronaphthalene with m.p.=113°-114° C. (ethyl ether) were separated by column chromatography on silica gel (eluent toluene:methanol=9:1).

EXAMPLE 8

Preparation of N-[2-(2,6-dichlorophenoxy)-ethyl]-N-propyl-2-amino-5-benzyloxy-6-hydroxy-1,2,3,4-tetrahydronaphthalene hydrochloride To a suspension of LiAlH$_4$ (0.1 g; 2.6 mmoles) in anhydrous tetrahydrofuran (50 ml), a solution of 2-[N-propyl-(2,6-dichlorophenoxy)-acetamido]-5-benzyloxy-6-hydroxy-1,2,3,4-tetrahydronaphthalene (1 g; 1.9 mmoles), prepared as described in example 7, in anhydrous tetrahydrofuran (10 ml) was added dropwise.

After 1 hour the excess of LiAlH$_4$ was decomposed with water (4 ml) and the formed salts were filtered.

After evaporation of the solvent a residue was obtained, dissolved in methanol and the solution was acidified with a solution of HCl in ethanol.

After evaporation N-[2-(2,6-dichlorophenoxy)-ethyl]-N-propyl-2-amino-5-benzyloxy-6-hydroxy-1,2,3,4-tetrahydronaphthalene hydrochloride was obtained as a chromatographically pure oil (thin layer chromatography, eluent methylene chloride: methanol:acetic acid=9:1:0.1).

$^1$H-NMR (60 MHz-CDCl$_3$): delta (ppm): 1.0 (3H, t); 1.6-2.1 (4H, m); 4.7 (2H, m); 5.2 (2H, s); 6.53-7.66 (10H, m).

EXAMPLE 9

Preparation of N-[2-(2,6-dichlorophenoxy)-ethyl]-N-propyl-2-amino-5-benzyloxy-6-O-dibezylphosphate-1,2,3,4-tetrahydronaphthalene To a solution of N-[2-(2,6-dichlorophenoxy)-ethyl]-N-propyl-2-amino-5-benzyloxy-6-hydroxy-1,2,3,4-tetrahydronaphthalene (3.8 g; 7.6 mmoles), prepared as described in example 8, in dimethylformamide (80 ml) a suspension (0.4 g) of 50% NaH in mineral oil was added.

After 2 hours at room temperature a solution of dibenzyl chlorophosphonate obtained by reacting N-chlorosuccinimide (1.52 g) and dibenzyl phosphite (3 g), in toluene (75 ml) was added dropwise in 2 hours at 20° C.

After further 4 hours the reaction mixture was poured into water and extracted with ethyl acetate. The organic phase was washed with water and dried on sodium sulphate. After evaporation of the solvent the residue was purified by column chromatography on silica gel (eluent methylene chloride:ethyl acetate=95:5) obtaining N-[2-(2,6dichlorophenoxy)ethyl]-N-propyl-2-amino-5-benzyloxy-6O-dibenzylphosphate-1,2,3,4-tetrahydronaphthalene as a chromatographically pure oil (thin layer chromatography, eluent methylene chloride:ethyl acetate=95:5).

$^1$H-NMR (60 MHz-CDCl$_3$): delta (ppm): 0.9 (3H, t); 1.21-2.2 (4H, m); 2.45-3.16 (8H, m); 4.1 (3H, t); 5.1-5.23 (6H, m); 6.9-7.46 (20H, m).

EXAMPLE 10

Preparation of N-[2-(2,6-dichlorophenoxy)-ethyl]-N-propyl-2amino-5-hydroxy-6-O-dihydrogenphosphate-1,2,3,4-tetrahydronaphthalene.

To a solution of N-[2-(2,6-dichlorophenoxy)-ethyl]-N-propyl-2-amino-5-benzyloxy-6-O-dibenzylphosphate-1,2,3,4-tetrahydronaphthalene (2 g; 2.63 mmoles), obtained as described in example 9, in ethanol 80% (60 ml) palladium 10% on activated charcoal (0.2 g) was added.

The reaction mixture was hydrogenated at room temperature under a pressure of 2-3 hydrogen atmospheres.

After 3 hours the suspension was filtered and the solution was evaporated.

The residue was crystallized from methanol giving N-[2-(2,6-dichlorophenoxy)-ethyl]-N-propyl-2-amino- 5-hydroxy-6-O-dihydrogenphosphate-1,2,3,4-tetrahydronaphthalene with a m.p.=225°-227° C.

EXAMPLE 11

Anti-hypertensive activity

The compounds of formula I, administered by intravenous route in spontaneously hypertensive rat at the dose of 0.033-0.53 μm/kg, induce a meaningful systemic arterial pressure decrease comprised between 20 and 90 mmHg.

The compound N-[2-(2,6-dichlorophenoxy)-ethyl]-N-propyl-2-amino-5,6-dihydroxy-1,2,3,4-tetrahydronaphthalene hydrochloride (Compound A) was tested by intravenous route in anesthetized dog in order to evaluate the effects on systemic arterial pressure. Compound A, administered by intravenous route at the doses of 10 and 20 μg/kg, reduced systemic arterial pressure as well as peripheral resistances and particularly femoral resistances, the last reduction being associated also with an increase of the corresponding haematic flow.

The results are reported in table 1.

TABLE 1

Effects of Compound A on arterial pressure, heart rate and vascular resistances.

| | Heart rate (beats/min) | Arterial pressure (mmHg) | | | a. renal flow (ml/min) | Renal resistances (mmHg/ml/min) | a. femoral flow (ml/min) | Femoral resistances (mmHg/ml/min) |
| --- | --- | --- | --- | --- | --- | --- | --- | --- |
| | | Mx | Md | Mn | | | | |
| Basal | 152 + 11 | 160 + 10 | 136 + 4 | 118 + 5 | 143.7 + 23.7 | 1.007 + 0.186 | 54.1 + 3.8 | 2.471 + 0.260 |
| Compound A 10 μg/kg iv | 161 ± 12 | 145 ± 8 | 119 ± 7 | 102 ± 8 | 144.7 ± 20.6 | 0.871 ± 0.162 | 67.4 ± 12.4 | 1.802 ± 0.471 |
| Basal | 136 + 13 | 148 + 8 | 132 + 8 | 118 + 9 | 129.9 + 31.8 | 1.246 + 0.389 | 65.6 + 20.0 | 2.445 + 0.787 |
| Compound A 20 μg/kg iv | 146 ± 17 | 124 ± 9 | 109 ± 9 | 96 ± 11 | 128.9 ± 31.3 | 1.082 ± 0.367 | 87.8 ± 20.0 | 1.274 ± 0.171 |

What we claim is:

1. A compound of formula $$\text{R—O} \underset{R_1O}{\overset{(CH_2)_n}{\bigcirc}} \underset{(CH_2)_m}{>} CH-(CH_2)_{\overline{p}} N - CH_{\overline{2}} CH_{\overline{2}} O - \bigcirc \underset{R_3}{\overset{R_2}{\underset{CH_2-CH_2-CH_3}{|}}} \quad (I)$$

wherein

R and $R_1$, the same or different, represent hydrogen atoms or acyl groups derived from optionally substituted aliphatic, aromatic or heteroaromatic carboxylic acids, from optionally substituted carbamic or carbonic acids, or from a phosphoric acid of formula $$R_4-O-\overset{\overset{O}{\|}}{\underset{OH}{P}}-$$

wherein $R_4$ represents a hydrogen atom, a $C_1-C_6$ alkyl optionally substituted by one or more groups selected from hydroxy, alkoxy, acyloxy, amino, carboxy and alkoxycarbonyl; or a phenyl; provided that when one of R and $R_1$ represents an acyl derived from phosphoric acid, the other represents a hydrogen atom;

the group O-R is bonded to one of the positions adjacent to the O-$R_1$ group; with the proviso that at most one of R and $R_1$ is hydrogen;

n and p each represents an integer selected between 0 and 1;

m represents an integer selected from 1, 2, 3 and 4 such that n+p=1 and m+n represent an integer selected from 2, 3 and 4;

$R_2$ and $R_3$, the same or different, represent a hydrogen or a halogen atom, an alkyl or an alkoxy group;

and their salts with pharmaceutically acceptable acids.

2. A compound according to claim 1, wherein R and $R_1$, the same or different, represent acyl groups derived from carboxylic acids selected from formic, acetic, propionic, butyric, isobutyric, valeric, pivalic, optionally substituted benzoic, and optionally substituted 2-pyridinecarboxylic, 3-pyridinecarboxylic, 4-pyridinecarboxylic acids.

3. A compound according to claim 1, wherein one of R and $R_1$ represents a hydrogen atom and the other represents an acyl derived from phosphoric acid of formula $$R_4-O-\overset{\overset{O}{\|}}{\underset{OH}{P}}-$$

wherein $R_4$ represents a hydrogen atom or a methyl or an ethyl group, optionally substituted by one or more groups selected from hydroxy, methoxy, acetoxy, amino, carboxy, methoxycarbonyl, ethoxycarbonyl and phenyl.

4. A compound, according to claim 1, wherein $m+n=3$.

5. A compound, according to claim 1, wherein R and $R_1$, the same or different, represent acyl groups derived from carboxylic acids selected from formic, acetic, propionic, butyric, isobutyric, valeric, pivalic, optionally substituted benzoic, and optionally substituted 2-pyridinecarboxylic, 3-pyridinecarboxylic, 4-pyridinecarboxylic acids.

6. A compound, according to claim 1, wherein one of R and $R_1$ represents a hydrogen atom and the other represents an acyl derived from phosphoric acid of formula $$R_4-O-\overset{\overset{O}{\|}}{\underset{OH}{P}}-$$

wherein $R_4$ represents a hydrogen atom or a methyl or an ethyl group, optionally substituted by one or more groups selected from hydroxy, methoxy, acetoxy, amino, carboxy, methoxycarbonyl, ethoxycarbonyl and phenyl.

7. A pharmaceutical composition containing a therapeutically effective amount of a compound according to claim 1 together with one or more pharmaceutically acceptable excipients.

8. A method for the treatment of hypertension, of cardiac insufficiency and decompensation and of cerebral and peripheral vascular diseases consisting in administering a therapeutically effective amount of a compound according to claim 1.

* * * * *